United States Patent
Nutten et al.

(10) Patent No.: US 10,478,472 B2
(45) Date of Patent: Nov. 19, 2019

(54) COMBINATION OF TOLEROGENIC PEPTIDES AND TFG-B FOR USE IN THE INDUCTION AND MAINTENANCE OF ORAL TOLERANCE IN YOUNG MAMMALS

(71) Applicant: NESTEC S.A., Vevey (CH)

(72) Inventors: Sophie Helene Nutten, Palezieux-village (CH); Nanda De Groot, Pully (CH); Valerie Francoise Verhasselt, Vallauris (FR)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/580,180

(22) PCT Filed: Jun. 10, 2016

(86) PCT No.: PCT/EP2016/063341
§ 371 (c)(1),
(2) Date: Dec. 6, 2017

(87) PCT Pub. No.: WO2016/198630
PCT Pub. Date: Dec. 15, 2016

(65) Prior Publication Data
US 2018/0140674 A1   May 24, 2018

(30) Foreign Application Priority Data
Jun. 12, 2015 (EP) .................... 15171942

(51) Int. Cl.
*A61K 38/18* (2006.01)
*A23L 33/00* (2016.01)
*A23L 33/17* (2016.01)
*A23K 20/147* (2016.01)
*A23K 50/40* (2016.01)
*A23K 50/60* (2016.01)
*A61K 38/01* (2006.01)
*A23L 33/18* (2016.01)
*A61P 37/08* (2006.01)

(52) U.S. Cl.
CPC ........ *A61K 38/1841* (2013.01); *A23K 20/147* (2016.05); *A23K 50/40* (2016.05); *A23K 50/60* (2016.05); *A23L 33/17* (2016.08); *A23L 33/18* (2016.08); *A23L 33/40* (2016.08); *A61K 38/018* (2013.01); *A61P 37/08* (2018.01); *A23V 2002/00* (2013.01)

(58) Field of Classification Search
CPC .......................... A61K 38/1841; A61K 38/018
See application file for complete search history.

(56) References Cited

U.S. PATENT DOCUMENTS 6,737,076 B2 * 5/2004 Fritsche .................. A23J 3/343
                                                            424/400
10,092,633 B2 * 10/2018 Blanchard ............ A61K 38/018

FOREIGN PATENT DOCUMENTS

| EP | 0322589    | 7/1989 |
| EP | 2044851    | 4/2009 |
| WO | 2015090347 | 6/2015 |

OTHER PUBLICATIONS

Madureira et al. "Bovine whey proteins—Overview on their main biological properties" Food Research International, 2007, vol. 40, pp. 1197-1211.
Pecquet et al. "Peptides obtained by tryptic hydrolysis of bovine β-lactoglobulin induce specific oral tolerance in mice" J Allergy Chin Immunol, 2000, vol. 105, No. 3, pp. 514-521.

* cited by examiner

*Primary Examiner* — Christina Bradley
(74) *Attorney, Agent, or Firm* — K&L Gates LLP (57) ABSTRACT

This invention relates to the administration of a combination of TGF-β and one or more peptides comprising specific sequences of β-lacto-globulin. The peptides are hypoallergenic but retain the capability to induce tolerance to the native protein. The combination of TGF-β and one or more of these peptides has the therapeutic effect of inducing and maintaining oral tolerance towards newly introduced proteins, in particular, at the weaning period. The combination can modulate the infant and toddler immune response to allergens.

10 Claims, 1 Drawing Sheet
Specification includes a Sequence Listing.

SEQUENCE LISTING

```
<160> NUMBER OF SEQ ID NOS: 8

<210> SEQ ID NO 1
<211> LENGTH: 6
<212> TYPE: PRT
<213> ORGANISM: Bos taurus

<400> SEQUENCE: 1

Ile Val Thr Gln Thr Met
1               5

<210> SEQ ID NO 2
<211> LENGTH: 7
<212> TYPE: PRT
<213> ORGANISM: Bos taurus

<400> SEQUENCE: 2

Lys Gly Leu Asp Ile Gln Lys
1               5

<210> SEQ ID NO 3
<211> LENGTH: 8
<212> TYPE: PRT
<213> ORGANISM: Bos taurus

<400> SEQUENCE: 3

Asp Ala Gln Ser Ala Pro Leu Arg
1               5

<210> SEQ ID NO 4
```

```
<211> LENGTH: 9
<212> TYPE: PRT
<213> ORGANISM: Bos taurus

<400> SEQUENCE: 4

Val Glu Glu Leu Lys Pro Thr Pro Glu
1               5

<210> SEQ ID NO 5
<211> LENGTH: 5
<212> TYPE: PRT
<213> ORGANISM: Bos taurus

<400> SEQUENCE: 5

Ile Ile Ala Glu Lys
1               5

<210> SEQ ID NO 6
<211> LENGTH: 8
<212> TYPE: PRT
<213> ORGANISM: Bos taurus

<400> SEQUENCE: 6

Ile Asp Ala Leu Asn Glu Asn Lys
1               5

<210> SEQ ID NO 7
<211> LENGTH: 6
<212> TYPE: PRT
<213> ORGANISM: Bos taurus

<400> SEQUENCE: 7

Val Leu Asp Thr Asp Tyr
1               5

<210> SEQ ID NO 8
<211> LENGTH: 9
<212> TYPE: PRT
<213> ORGANISM: Bos taurus

<400> SEQUENCE: 8

Glu Val Asp Asp Glu Ala Leu Glu Lys
1               5
```

COMBINATION OF TOLEROGENIC PEPTIDES AND TFG-B FOR USE IN THE INDUCTION AND MAINTENANCE OF ORAL TOLERANCE IN YOUNG MAMMALS

CROSS REFERENCE TO RELATED APPLICATIONS

The present application is a National Stage of International Application No. PCT/EP2016/063341, filed on Jun. 10, 2016, which claims priority to European Patent Application No. 15171942.4, filed on Jun. 12, 2015, the entire contents of which are being incorporated herein by reference.

FIELD OF THE INVENTION

This invention relates to the administration of a combination of TGF-β and one or more peptides comprising specific sequences of β-lactoglobulin. The peptides are hypoallergenic but retain the capability to induce tolerance to the native protein. The combination of TGF-β and one or more of these peptides has the therapeutic effect of inducing and maintaining oral tolerance towards newly introduced proteins, in particular, at the weaning period. The combination can modulate the infant and toddler immune response to allergens.

BACKGROUND TO THE INVENTION

Food allergies, the first of which to occur in life is generally cows' milk allergy, are caused, in most cases, by a reaction to proteins in food. In the early years of life the immune system is still developing and may fail to develop tolerance to dietary antigens (this may also be described as insufficient induction of oral tolerance). The result is that the baby or child or young animal has an exaggerated immune response to the dietary protein and develops an allergic response to it. Food allergies may affect not only humans, but also other mammals such as dogs and cats.

Usually, food hypersensitivity develops just after a susceptible baby, child or young animal first encounters a new food containing potential allergens. Apart from its mother's milk (which can contain food proteins from the mother's diet), the first dietary proteins generally encountered by human babies at least, are cow's milk proteins. Cows' milk allergy (CMA) is the most common food allergy in human babies, affecting approximately 2.5% of all infants [Sicherer S H et al. (2010), Food allergy, Sampson H A, *J. Allergy Clin. Immunol.* (125)]. Approximately 85% of children out-grow their allergy to cow's milk before the age of 2 to 3 years old. As such, CMA affects other age groups with a lower prevalence.

It is generally accepted that babies with established cows' milk allergy have an increased risk of developing allergies to other dietary proteins such as egg and cereal proteins. These allergies may manifest themselves clinically as atopic diseases such as atopic dermatitis, eczema and asthma. Even those babies who have successfully developed oral tolerance to cows' milk proteins may subsequently develop allergies to other dietary proteins such as egg and cereal proteins when these are introduced into the diet at weaning.

Besides breastfeeding, the primary recommendation for prevention of CMA is the use of partially hydrolyzed hypoallergenic formulae, which are recommended to be prescribed to "at risk" asymptomatic infants, with atopic parents. This approach has been demonstrated to be efficient in preventing sensitization by hydrolyzed proteins (peptides) and residual native (full length) proteins that are present (albeit in a much lower quantity than that in a non-hydrolyzed formula) in the formulae.

Thus, European patent application EP 2 332 428 discloses a formulation comprising a cow's milk peptide-containing hydrolysate capable of inducing oral tolerance. The peptides in question were identified as coming from bovine casein.

There are currently many examples of casein or whey-based partially hydrolyzed hypoallergenic formulae (e.g. NAN®-HA, BEBA®-HA, from Nestlé, and S26®-HA from Wyeth Infant Nutrition) on the market.

For infants already displaying symptoms of CMA, extensively hydrolyzed formulae (e.g. Alfare™, Altéra™ from Nestlé), non-allergenic milk substitute formulae, such as free amino acids (e.g. Alfamino™ from Nestlé) or soy based formulas (such as S26®-Soy, NURSOY™ from Wyeth Infant Nutrition, New York, and NESTLÉ® Good Start® ALSOY® from Nestlé) may be suitable alternatives to cow's milk standard or partially hydrolyzed formulae.

Thus, the primary focus to date in providing nutrition for children with allergies to cow's milk has been to find preparations which will not induce an allergic response, i.e. to provide non-allergenic formulations. One of the drawbacks of administering non-allergenic formulae (containing either free amino acids or extensively hydrolyzed cow's milk proteins) or soya based milk, to infants is that, while such formulations allow infants who are allergic to cow's milk to avoid an allergic response, they do not allow those children to develop oral tolerance to the cow's milk protein allergens so that they can go on to drink unaltered milk products later in life.

Oral tolerance is the specific suppression of cellular and/or humoral immune reactivity to an antigen by prior administration of the antigen by the oral route. It is an important part of the development of the immune system in the first months of life and allows the infant to consume food without adverse reaction. Failure of the establishment of oral tolerance leads to allergy. The development of oral tolerance is linked to the normal immune system education, resulting in a reduced reaction to food antigens.

Several factors have been identified as affecting the induction and maintenance of oral tolerance, among these, the structure of the food protein, the dose and frequency of the antigen administration, as well as the immune status of the host.

To a certain extent, oral tolerance can be induced in infants via breastfeeding [Mosconi E, et al. (2010) Breast milk immune complexes are potent inducers of oral tolerance in neonates and prevent asthma development. Mucosal Immunol; 3:461-74 and Verhasselt et al (2008) Breast milk mediated transfer of an antigen induces tolerance and protection from allergic asthma, Nat Medecine; 14(2): 170-5]. Thus, infants who are breastfed by mothers who have been exposed to and immunized against certain allergenic foods like egg, nuts etc. develop oral tolerance towards these allergens.

Thus, there is a need to further identify the factors that may influence induction of oral tolerance. It is highly desirable to provide hypoallergenic or non-allergenic compositions having an ability to induce and maintain oral tolerance in the infant, to be administered particularly at the weaning period when young mammals are being introduced to new foods.

There is a need to provide nutritional solutions that can prevent or alleviate the development of allergies, especially in infants and toddlers, especially those who are at risk of developing allergy. There is a need to induce tolerance to a variety of allergens including milk, egg, (tree) nuts, peanuts, shellfish, wheat and soy. There is a need to prevent or alleviate the development of allergy during the weaning period when the latter allergens are introduced. There is a need to maintain oral tolerance that has been induced to certain allergens via maternal milk.

There is a need to design and produce nutritional interventions, especially via synthetic ingredients or combinations of ingredients, that can be administered to infants and toddlers, early in life and that reduce the probability or the magnitude of being or becoming allergic or developing allergies later in life.

This need exists for the general population of infants and toddlers and also for sub-populations of infants and toddlers having predisposition to allergies or having declared allergies.

There is a general need to provide relief from allergies or allergy symptoms and to develop means of inducing and maintaining the tolerance to common allergens, such as milk including milk, egg, (tree) nuts, peanuts, shellfish, wheat and soy especially in infants and toddlers.

SUMMARY OF THE INVENTION

The invention relates to a composition comprising a combination of at least one tolerogenic peptide that is between five and twelve amino acids in length and TGF-β. The tolerogenic peptides are described in PCT/EP2013/076643 and WO2000/42863 and were demonstrated to induce tolerance to milk proteins, in particular β-lactoglobulin.

TGF-β is a bioactive peptide present in both colostrum and, to a lesser extent, in mature breast milk. It has been identified as a potential regulator of atopic disease and it has been demonstrated that TGF-β-1 is significantly less secreted in mature milk of allergic mothers, compared to non-allergic mothers [Rigotti E et al., (2006) "*Transforming growth factor-beta and interleukin-10 in breast milk and development of atopic diseases in infants*." Clin Exp Allergy. 36(5):614-8]. In international patent application WO2009/040310, it is described how TGF-β was administered for the primary prevention of allergic reactions to newly introduced dietary protein in young mammals at the weaning period.

TGF-β is also present in bovine milk; its presence has been detected in various cow's milk fractions and commercial non hydrolyzed infant formula products (e.g. NAN® from Nestlé). However, TGF-β is lost during processing of hydrolyzed infant formula.

In the composition of the current invention, the combination of TGF-β and the tolerogenic peptide(s) results in a composition that modulates the mammalian immune response to allergens, during and after the weaning period when new foods are introduced to the young mammal. The composition can induce oral tolerance to milk proteins, in particular, β-lactoglobulin (BLG) and also can prolong this acquired oral tolerance to BLG as well as prolonging oral tolerance to other food proteins that has been acquired via the consumption of maternal milk. In particular, the oral tolerance may be prolonged wherein the young mammal has been fed maternal milk from a mother who has already been exposed to and/or sensitized to allergens, such as milk, or egg, or (tree) nut, or peanut, or shellfish, or wheat or soy, or any other food protein.

In human infants, administration of the composition of the invention during the weaning period will (i) induce and prolong oral tolerance to BLG by the presence of the peptides and TGF-β, (ii) at weaning, prolong the oral tolerance to food proteins that has been acquired by the infant or toddler through breast feeding.

The composition may be administered to mammals, especially to young infants and toddlers who are at risk of food allergy, including allergy to milk proteins, to induce oral tolerance to cow's milk, and to maintain tolerance to cow's milk as well as maintaining breast feeding induced oral tolerance to a broad range of proteins once weaning begins.

The peptides may also be used to induce tolerance to goat's and buffalo's milk proteins, especially β-lactoglobulin.

The composition may be administered in its pure form; diluted in suitable liquid, or in the form of a pharmaceutical composition, a nutritional composition or nutritional supplement.

According to an embodiment of the invention the peptide(s) in the composition is/are in the form of (i) isolated peptidic fractions from the hydrolysis of proteinaceous material containing BLG, and/or (ii) synthetically prepared peptides.

According to an embodiment of the invention the TFG-β in the composition is in the form of a whey or casein protein isolate naturally containing or enriched in TGF-β.

A major advantage of this composition is to induce and maintain oral tolerance to cow, sheep, buffalo or goat milk proteins, in particular to β-lactoglobulin, in mammals. Furthermore, oral tolerance that has been acquired in these mammals via maternal milk may be extended in time, through and beyond the critical weaning period by consumption of the composition of the invention.

These mammals may be young mammals, and particularly human infants or toddlers, "at risk" of developing food allergies, in particular, cow's milk allergy, having at least one parent or sibling who has allergies, or not "at risk". Thus, the compositions of the invention are of benefit to the general population of young mammals.

The composition may be administered to companion animals, for example dog and cats.

In a preferred embodiment, the composition comprises at least one peptide that is from five to twelve amino acids in length and comprises one of the peptide sequences SEQ ID No.1 to SEQ ID No.8, in the form of peptidic fractions. The dose of peptide(s) that may be administered to the young mammal, or adult mammal, may be between 0.4-50 umol/per kg body mass/day, preferably from 0.9-40 µmol/per kg body mass/day.

The dose of TGF-β that may be administered to the young mammal, may be between 600-4000 ng/per kg bodymass/day, preferably from 900-1600 ng/per kg bodymass/day and more preferably from 950-1300 ng/per kg bodymass/day.

The administration of the composition is preferably during the weaning period but it may take place before the weaning period has started. In humans, administration may start from birth, or from one, two, three, four, five or six months old, or at or just before the first time non-human milk is introduced into the infant's or toddler's diet. The composition is generally administered every day, or every second day. However, the administration may also be less regular for example, every third day. The administration period may be for at least one month, preferably, at least three months and, more preferably, for at least 6 months or up to one year. The administration may be for longer, for example up to three years.

The composition may be added to a base composition that is, for example, a human milk fortifier, starter infant formula, or a follow-up infant formula or a growing up milk.

The base composition may be a "non-allergenic" or a "hypoallergenic" composition.

The composition may be administered in a composition comprising further ingredients or prebiotics, preferably selected from 2'Fucosyllactose, Lacto-difucotetraose, 3Fucosyllactose, Lacto-N-fucopentaose I, Lacto-N-fucopentaose II, Lacto-N-fucopentaose III, Lacto-N-neotetraose, Lacto-N-tetraose, 3'Sialyllactose, 6'Sialyllactose, 3'Sia lyl-lacto-N-tetraose, 6'Sialyl-Lacto-N-neotetraose, inulin, fructooligosaccharide (FOS), short-chain fructooligosaccharide (short chain FOS), inulin, galacto-oligosaccharide (GOS), xylooligosaccharide (XOS), glanglioside, partially hydrolyzed guar gum, acacia gum, soybean-gum, or mixtures thereof.

The peptides may be administered in a composition comprising further ingredients or probiotics, preferably selected from *Lactobacillus paracasei, Lactobacillus rhamnosus, Bifidobacterium longum, Bifidobacterium lactis*, and *Bifidobacterium breve*.

BRIEF DESCRIPTION OF THE DRAWINGS

Statistical significance between specified groups using Mann-Whitney non parametric test is indicated by the p values written above the compared columns.

DETAILED DESCRIPTION

In the present invention, the term "tolerance" is to be understood as a state of specific immunological unresponsiveness. Both humoral (antibodies) and cell-mediated (lymphocytes etc.) pathways of the immune response may be suppressed by tolerance induction. A breakdown of oral tolerance is considered to be the underlying cause of food allergy.

The term "allergen" is to be understood as a protein or peptide capable of initiating allergic reactions in mammals, particularly in "at risk" young mammals, including infants and toddlers. Young infants and toddlers are considered being "at risk" of protein allergy when either at least one parent or sibling is atopic.

The term "tolerogenic peptides" is to be understood as proteic fragments, corresponding to parts of the native protein, sized from 300 to 6000 Da (3 to 50 amino acids), and preferably between 500 to 3000 Da, and more preferably between 500 and 1400 Da and being able to induce specific oral tolerance to native proteins.

The term "non-allergenic" composition is to be understood as a composition having a nitrogen source containing a well-balanced amino-acid composition. The "non-allergenicity" is defined for milk proteins as residual whey proteins not exceeding 1 ppm and as residual total caseins not exceeding 10 ppm.

The term "hypoallergenic composition" is to be understood as a composition that has low allergenicity.

The term "sensitized to" means has developed allergen-specific IgG1 and/or IgE antibodies after exposure to an allergen.

The term "extent of hydrolysis" means the extent to which the protein fraction in the composition is hydrolyzed. The extent of hydrolysis can be measured using a reagent such as trinitrobenzenesulfonic acid (TNBS) which reacts with the free amino nitrogen groups in protein hydrolysates. For hydrolysates based on whey protein, in "partial" protein hydrolysates, the TNBS reactive Nitrogen (expressed as % amino-N/TN) is usually within the range from 8-15% and in general, extensive protein hydrolysates are characterized as having a TNBS reactive Nitrogen % amino N/TN of 30-45%.

The term "weaning" means the introduction of human breast milk substitutes (such as infant formula) and/or complementary liquid or solid foods.

The term "infant" means a child in the earliest period of life, from birth up until he or she can walk (usually around one 12 months).

The term "toddler" means a young child, usually one between the ages of one and two and a half.

"TGF-β" or "transforming growth factor-beta" designates a group of at least five distinct but closely related bioactive peptides designated TGF-β1, TGF-β2 etc. and found inter alia in human milk (TGF-β1 and TGF-β2) (Li et al, Transforming Growth Factor-B Regulation of Immune Responses, Annu. Rev. Immunol. 2006 24:99-146). TGF-β is highly conserved between species (greater than 98% amino acid sequence homology).

The current invention relates to a composition comprising a combination of at least one of a specific set of tolerogenic peptides derived from BLG that are between 5 and 12 amino acids in length, and TGF-β, for use in the primary prevention of allergic reactions to milk proteins and to newly introduced dietary protein in a young mammal at weaning.

At least one peptide that is between five and twelve amino acids in length and comprising one of the sequences SEQ ID No 1-8, is present in the composition of the invention. The peptide sequences SEQ ID No 1-8 are shown in Table 1. The identification and characterization of the tolerogenic peptide sequences SEQ ID No 1-5, are described in International patent application PCT/EP2013/076643.

All sequences are listed in ASCII file Sequence Listing—PatentIn_ST25—3712036.03029, Size 1,760 bytes, and Date of Creation Jan. 26, 2018.

| SEQ ID No. | Sequence | Position in BLG Sequence |
|---|---|---|
| 1 | IVTQTM | 18-23 |
| 2 | KGLDIQK | 24-29 |
| 3 | DAQSAPLR | 49-56 |
| 4 | VEELKPTPE | 59-67 |
| 5 | IIAEK | 87-91 |

-continued

| SEQ ID No. | Sequence | Position in BLG Sequence |
|---|---|---|
| 6 | IDALNENK | 100-107 |
| 7 | VLDTDY | 110-115 |
| 8 | EVDDEALEK | 143-151 |

Peptides SEQ ID No. 6, IDALNENK, SEQ ID No. 7, VLDTDY, and SEQ ID No. 8 EVDDEALEK were previously identified in WO2000/42863 as being inducers of oral tolerance. The peptides were identified as part of a longer peptide sequence in the latter document.

In PCT/EP2013/076643, the inventors, using a cellular based assay with human cells expressing the Major Histocompatibility Complex (MHC) class II receptor, HLA-DR, identified the peptide sequences of Table 1, present in a partially hydrolyzed infant formula NAN®-HA (otherwise known as BEBA® HA from Nestlé), as being those that bound to the HLA receptor.

In that patent application, it was explained how, as the first step in the induction of oral tolerance, the HLA receptor presents peptide sequences to the T cells, thereby inducing tolerance. Thus, development of tolerance is largely dependent on the recognition of the peptide sequence by the MHC. The peptide binding regions of the MHC recognize peptide sequences or assembly of peptides composed of, on average, ten amino acids with a minimum number of five. The penta-peptides can be included in longer peptide sequences (or even proteins), as they will be digested in the gastrointestinal tract to lead to this smaller peptide size of 5-18 amino acids. This explains, in part, why extensively hydrolyzed products composed of free amino acids, di-peptides, tri-peptides, and tetra-peptides do not induce oral tolerance.

The ability of the peptides of Table 1 to induce oral tolerance in vivo was further confirmed in PCT/EP2013/076643 in an experimental mouse model of sensitization to BLG.

The peptide or peptides included in the composition of the current invention have an amino acid length of from five to twelve and each peptide comprises a sequence chosen from SEQ ID No.1-8 (see Table 1). The peptide(s) thus, has/have a specific length (5-12 amino acids).

Peptides shorter than pentamers (five amino acids in length) may not provide the tolerogenic effect, whereas peptides that are longer than 12-mers are thought to have an increased risk of allergenicity.

Thus, the peptide may be a 5-mer, 6-mer, 7-mer, 8-mer, 9-mer, 10-mer, 11-mer or a 12-mer comprising any one of the sequences selected from SEQ ID No. 1-8. Thus, the peptide may be any peptide that is a 5-mer, 6-mer, 7-mer, 8-mer, 9-mer, 10-mer 11-mer or a 12-mer comprising the sequence IVTQTM (SEQ ID No. 1) or IVTQTM (SEQ ID No. 1), or KGLDIQK (SEQ ID No. 2), or DAQSAPLR (SEQ ID No. 3), VEELKPTPE (SEQ ID No. 4), IIAEK (SEQ ID No. 5), IDALNENK (SEQ ID No. 6), VLDTDY (SEQ ID No. 7), or EVDDEALEK (SEQ ID No.8).

The peptides included in the composition of the invention may be a combination of any one, or two, or three, or four, five, six, seven or all eight of the peptides comprising sequences SEQ ID No.1-8.

According to one embodiment of the invention, the isolated peptides may be synthetically made, according to standard methods known to the skilled person. Alternatively, according to another embodiment of the invention, they may be concentrated, or extracted from natural sources such as milk (e.g. bovine milk) or milk fractions which have been preferably modified, treated to, for example, produce or concentrate the peptides. Milk hydrolyzates, in which milk proteins have been hydrolyzed by enzymes or other means, may be generated by methods known in the art. Methods for extracting, separating and identifying the peptidic fractions containing the peptides of the invention, from milk hydrolyzates, are also known to the skilled person. The peptides of the invention may be generated by these methods.

The preparation and characterization of the peptides SEQ ID No. 1 to 5 are described in detail in PCT/EP2013/076643. The methods described therein may be used to prepare the peptides for inclusion in the composition of the invention. The preparation and characterization of the peptides SEQ ID No. 6 to 8 are described in detail in WO2000/42863.

According to one embodiment of the invention, the dose of peptide(s) administered is in the range of 0.4-50 µmol/per kg bodymass/day, preferably from 0.9-40 µmol/per kg bodymass/day. For example, if the peptides are administered as part of an infant formula, the peptides may be present in the formula at a concentration of 50-150 µg/g powder. A typical dosage of infant formula for an infant of five month-old baby would be three bottles per day of seven scoops of powder each, and for a six month-old baby or older, two bottles per day of seven scoops each. The doses are based on an average baby weight for a six-month-old being about 8 kg, and for a twelve-month-old being about 9.5 kilos.

It was described in PCT/EP2013/076643 that sequences SEQ ID No.1-5 were identified as being highly conserved (100% sequence identity) in BLG in cow, buffalo, domestic goat, sheep and mouflon. Thus, it is believed that any of these sources of milk containing these sequences can induce oral tolerance to bovine milk and vice versa. Thus, the inventors postulate that peptides identified by the inventors can induce oral tolerance to BLG from any of these sources.

According to one embodiment of the invention, the composition of the invention is administered in an amount sufficient to induce oral tolerance, preferably complete oral tolerance to bovine BLG. The BLG may also be from sheep, or goat. Complete oral tolerance is taken to mean no allergic reaction is observed after a DBPCFC (double blind placebo controlled food challenge) performed with cow's milk, in particular bovine BLG.

According to one embodiment of the invention, the peptides may be present in an amount of 0.01% to 5%, and preferably 0.1% to 0.5% of total protein.

The composition of the invention also comprises TGF-β.

The TGF-β may be in the form of a polypeptide growth factor isolated from milk as described for example in EP 313515 or WO 92/00994. Alternatively, a recombinant TGF-β may be used, if preferred.

Furthermore, TGF-β is present in both whey and casein fractions of mammalian milk in a predominantly active form. Thus, the TGF-β to be included in the composition of the invention may be in the form of a whey or casein fraction coming from mammalian milk, for example, from cow, goat, buffalo, or camel milk.

Milk fractions containing TGF-β that may be used in the invention are a whey protein fraction containing TGF-β available under the name TM0301™, Protarmor 865 SB™, or Vitalarmor from Armor Proteines, France, or XP-828L™ from Advitech, Canada.

According to an embodiment of the present invention, the composition of the invention is a human milk fortifier, an infant formula, preferably, a follow-on formula, containing from 12 to 300 ng TGF-β per gram of dry composition, preferably between 45-100 ng TGF-β per gram of dry composition, more preferably 65-85 ng TGF-β per gram of dry composition.

According to one embodiment of the invention, the dose of TGF-β administered is in the range of 600-4000 ng/per kg bodymass/day, preferably from 900-1600 ng/per kg bodymass/day and more preferably from 950-1300 ng/per kg bodymass/day.

Preferably, the composition, according to an embodiment of the invention, contains both TGF-β1 and TGF-β2. Preferably the TGF-β1 and TGF-β2 are in a ratio between 2:1 and 1:20, more preferably in a ratio between 1:10 and 1:20, for example 1:16.

The composition may be administered orally directly to the young mammal alone (pure or diluted in water or mother's milk, for example) or as a composition that is an infant milk formula, follow-on formula or growing up milk, or a food supplement, for example, a human milk fortifier. It may also be administered in any milk support used during trophic feeding, non-milk based infant formulas, a baby cereal or yoghurt, a baby meal pudding of cheese, a dairy or fruit drink, a smoothy, a snack or biscuit or other bakery item. It may also be administered in pet food and beverage such as any dry food or kibble, wet food or canned form, or supplement.

According to one embodiment of the invention, the composition is administered in a hypoallergenic or non-allergenic composition. It may be administered, for example in a hypoallergenic human milk fortifier, premature infant formula, starter infant formula, follow-on formula, food supplement or a growing up milk. It may be administered, for example in a non-allergenic human milk fortifier, premature infant formula, starter infant formula, follow-on formula, food supplement or a growing up milk. Hypoallergenic and non-allergenic compositions usually contain partially or extensively hydrolyzed protein isolates. In a preferred embodiment the composition is administered in a hypoallergenic composition comprising a milk hydrolysate having an extent of hydrolysis of between 8 and 15%. In the case where the protein fraction of the composition is present as a partial or extensive hydrolysate, the TGF-β may added separately to ensure that the full length (unhydrolyzed) TGF-β (TGF-β1 and TGF-β2 are present in the composition.

On the other hand, according to one embodiment of the invention, if the composition contains a non-hydrolyzed (for example, whey) protein fraction, then few or no further additions of TGF-β may be required to bring the TGF-β content to the required level. According to the embodiments of the invention wherein the protein isolate of the composition is not hydrolyzed, or is extensively hydrolyzed, the tolerogenic peptides comprising sequences SEQ ID No.1-8 are added separately to the composition. The tolerogenic peptides comprising sequences SEQ ID No.1-8 may also be added separately to the composition, in the case of a hypoallergenic composition comprising a partially hydrolyzed protein isolate.

The compositions of the invention may be used in the indicated dosage as a nutritional solution or medicament to prevent allergic reactions to newly introduced dietary protein in a young mammal at weaning. Thus, in particular, the compositions are used to induce oral tolerance to BLG (from any of cow, buffalo, domestic goat, sheep and mouflon) and also to maintain oral tolerance that has been acquired to BLG or to other food proteins via the consumption of maternal milk by the young mammal.

The indicated therapeutic effect is obtained by feeding the composition to the young mammal during and, optionally, before the weaning period. Such compositions may be administered to infants and toddlers or sub-population of infants and toddlers presenting symptoms or susceptibility to allergies.

The oral tolerance to BLG that is induced by the composition of the invention may provide relief from allergies in the medium term (during the treatment or within 1, 6, 12 or 18 months after the treatment).

Additionally, the prolongation or maintenance of oral tolerance that has been acquired by the consumption of maternal milk, leads to the prevention of the development of allergic symptoms to newly introduced foods during the weaning period. It is known that oral tolerance that has been acquired through the consumption of breast milk is lost after a certain period (for example 12 weeks in mice [Mosconi et al (2010)]). Thus, prolonging or maintaining this already acquired oral tolerance for as long as possible is a highly effective way to reduce the occurrence of food allergy and atopic disease.

This effect is demonstrated in the ovalbumin allergy mouse model experiment of Example 1. In this example, groups of mouse pups, at weaning, were fed either (i) water (ii) NAN®-HA formula or (iii) TGF-β enriched NAN®-HA formula. Regimen (iii) is a composition according to an embodiment of the invention. NAN®-HA contains all 5 peptides SEQ ID 1-5. The mouse pups in each of the three regimen groups were further divided into two sub groups depending on whether they had been breastfed by naïve (not having been exposed to ovalbumin) mothers, or by mothers who had been exposed and immunized to ovalbumin (OVA).

The mouse pups were then submitted to a protocol of food allergy induction consisting briefly in ovalbumin/aluminium hydroxyde (adjuvant) intraperitoneal injection followed by oral OVA challenges. Their allergy symptoms, in particular, diarrhea, were then measured (Experiment 1). A second set of OVA challenges was performed (Experiment 2) and allergy symptoms, in particular diarrhea, were measured again.

Figure 1:
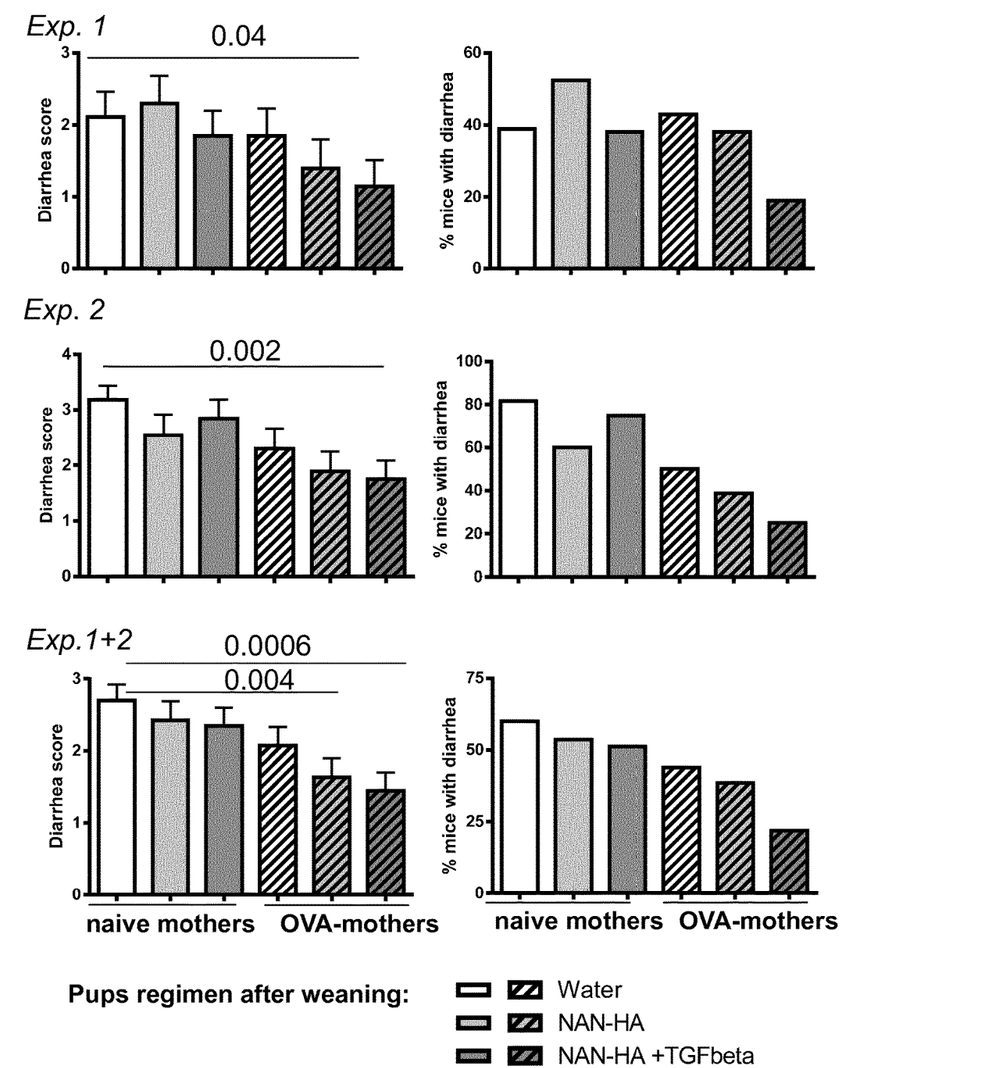
FIG. 1: Food allergic diarrhea. Six groups of mice were tested for their susceptibility to food allergic diarrhea at 12 weeks: mice breastfed by nave mothers (open columns) or by OVA-exposed and immunized mothers (hatched columns) that received orally during 9 weeks after weaning either water (white), NAN®-HA (grey) or TGF-beta enriched NAN®-HA (dark grey). The experiment has been performed twice; in Exp. 1, there are 6 mice per group and in Exp. 2, 10-11 mice per group. On the left panel, data represent mean+sem of diarrhea score observed during the last 3 challenges with ovalbumin (Exp.1) and 2 challenges (Exp.2); on the right panel, data represent % of mice displaying diarrhea during OVA challenges (score superior or equal to 3) during the last 3 (Exp.1) or 2 challenges (Exp.2).

FIG. 1 shows the results of this experiment and demonstrates that, in the two experiments performed, susceptibility to food allergic diarrhea is significantly decreased at 12 weeks in the sole group of mice that were breastfed by mothers exposed and immunized to OVA and that received TGF-β enriched NAN®-HA enriched formula after weaning, as compared to mice breastfed by nave mothers and receiving water after weaning (control group).

When analyzing both Experiment 1 and Experiment 2 together, only 22% of mice experienced diarrhea upon OVA challenge in the group of mice breastfed by OVA exposed mother and that further received NAN®-HA enriched in TGF-β, versus 60% of mice breastfed by nave mothers and receiving water. 43% of mice who had been breastfed by OVA exposed mothers and received water after weaning experienced diarrhea.

In the second experiment, where food allergy was more severe than in first experiment, there was an even better protection than in Experiment 1. Indeed, 80% of mice had allergic diarrhea in the last 2 challenges in the control group, while only 25% experienced diarrhea in the group of mice breastfed by mothers immunized and exposed to OVA and that received TGF-β enriched NAN®-HA after weaning.

When pooling the results obtained in the 2 experiments, a statistically significant protection was also observed in the group of mice breastfed by mothers immunized and exposed to OVA and receiving NAN®-HA formula at weaning; in this case protection was however less reproducible and less profound than the one observed in mice breastfed by mothers immunized and exposed to OVA and receiving TGF-β-enriched NAN®-HA enriched formula at weaning.

In data not shown here, it has also been observed that oral tolerance is induced and prolonged in pups fed by mothers who were exposed to the allergen while feeding their pups (i.e. during the feeding period), but who were not sensitized to the allergen. The effect was less marked compared to that observed in pups that had been fed by mothers who were exposed to and sensitized to the allergen. Thus, in general, the composition of the invention induces oral tolerance to BLG and prolongs the oral tolerance to food allergens that has been induced by the consumption of maternal milk from mothers who were exposed to, but not necessarily sensitized to these food allergens. The exposure to the food allergen by the mother is generally during the feeding period. Generally, administration of the composition of the invention to the young mammal at weaning prolongs oral tolerance to food allergens in young mammals who have been fed milk from a mother who has been exposed to and, optionally, sensitized to those food allergens, generally, during the feeding period. The food allergens may be for example milk, or egg, or (tree) nut, or peanut, or shellfish, or wheat or soy, or any other food protein. The prolongation of oral tolerance is greater in those young mammals who are already fed by mothers who are already sensitized to the food allergen.

NAN®-HA enriched with TGF-β is an example of one embodiment of the composition of the invention suitable for administration to infants.

Thus, the applicants have demonstrated that the composition of the invention prolongs/maintains oral tolerance towards allergens that has been induced by maternal milk consumption, and prevents development of allergic symptoms in the young mammal upon exposure to these allergens during the weaning period.

The composition according to the invention also has the capacity to induce oral tolerance to BLG, irrespective of whether or not the young mammal to whom the composition is administered has consumed milk from a mother who has been exposed to and sensitized to BLG.

The composition also has the capacity to maintain oral tolerance that the young mammal has acquired from consuming maternal milk from a mother who has already been exposed to and optionally sensitized to allergens, in particular milk, or egg, or (tree) nut, or peanut, or shellfish, or wheat or soy, or any other food protein.

According to an embodiment of the invention the composition may be administered for use in the primary prevention of allergic reactions to milk proteins and to newly introduced dietary protein in a young mammal during and after weaning. According to an embodiment of the invention the composition may be administered for use in the primary prevention of atopic diseases in a young mammal during and after weaning. According to one embodiment the young mammal is at risk of developing allergy.

The administration of the composition is preferably during the weaning period when new foods are introduced to the young mammal. Administration may however take place before the weaning period has started to "prime" the immune system. In humans, if the mother breastfeeds exclusively from birth, the weaning period often takes place at about four, or five or six months of age. If, on the other hand, the mother does not exclusively breastfeed from birth, the weaning period (when foods other than breast milk are introduced) may also take place earlier, at one, two or three months or even at one or two or three weeks, or even from birth.

So that the composition of the invention exerts a maximum therapeutic benefit, its administration should be regular and often, for example, every day, or every second day. However, the administration may also be less regular for example, every third day.

Administration may be at least once a day. It may be with every feeding time or less often. It may be, for example, once or twice or three time or four times or five times or more a day. The number of times per day that the composition is administered also depends on the infant or toddler's age, how often he/she feeds and the care giver's wishes.

The administration period may be for at least one month, preferably at least three months and more preferably, for at least six months or up to one year. The administration may be for longer, for example up to three years.

The period of administration of the peptides of the invention can be continuous or discontinuous. Continuous administration is preferred for a more sustained effect. However, it is thought that a discontinuous pattern (for example, every second day, or daily administration during one week per month, or during alternate weeks) can induce positive effects on the young mammal or adult.

Preferably, the administration is by daily intake (to be taken once or several times a day), or by weekly intake (to be taken four or three times or twice or once a week).

The combination of the tolerogenic peptide(s) comprising any of the sequences SEQ ID No. 1-8 and TGF-β can be administered alone without other compounds, pure or diluted in water or milk, including human breast milk for example or in a mixture with other compounds (such as dietary supplements, nutritional supplements, medicines, carriers, flavours, digestible or non-digestible ingredients).

The combination may be administered, for example, to a young infant or toddler, as part of a composition that is a human milk fortifier, or other nutritional supplement. The composition comprising the combination of peptide(s) and TGF-β may also be administered in a pharmaceutical composition.

According to one embodiment of the invention, the combination of peptide(s) and TGF-β peptides may be added to, or be comprised into a base composition that is a composition intended for mammals, particularly human and pets. The base composition may contain intact (non-hydrolyzed) proteins. The base composition may be an infant formula, a follow-up formula, or a nutritional composition for infants or toddlers.

According to one embodiment of the invention, the combination of peptide(s) and TGF-β peptides may be added to, or be comprised into a base composition that is a hypoallergic composition intended for mammals, particularly human and pets. Thus, the base formula to which the peptides are added, or in which the peptides may be contained, may be, for example, a hypoallergenic (HA) formula in which the milk proteins are partially hydrolyzed. It may also be a non-allergenic formula in which the milk proteins are extensively hydrolyzed or are replaced by free amino acids, or a cow milk substitute such as soya based. It may, for example, be an infant formula, a follow-up formula, or a nutritional composition for infants or toddlers with particular physiological/pathological conditions.

In one embodiment, the formula is an elemental infant formula and the base formula comprises no peptides or proteins but only amino acids.

In one embodiment the proteins or peptides of the base formula originate, in part or in full, from intact sweet whey or sweet whey hydrolysate from which the cGMP have been removed. Reference is made in that regard to EP880902 whereby a process allows the removal of practically all the caseino-glyco-macropeptide (a fraction rich in threonine and poor in tryptophan) from bovine whey thereby increasing the alpha-lactalbumin proportion (a fraction very rich in tryptophan). By combining this modified sweet whey fraction with skim milk, and with the addition of some free L-histidine and L-arginine (in order to reach the minimum amounts of these amino acids required by EC Directive), the formulation has an amino acid profile much closer to that of human milk, characterised in particular by comparable tryptophan and threonine levels, allowing the adaptation of its protein content to that of human.

When administered together with the above described optimized peptide profile, it is understood that the combination of peptide(s) and TGF-β can act synergistically with the optimized amino acid profile to deliver the induction and maintenance of oral tolerance while providing the optimized protein nutritional value (that may boost the effect of the peptides and TGF-β by fulfilling the protein needs in the most proper quantitative way).

The peptides of the composition of the invention may be administered, for example, as part of an infant formula at a concentration of 50-150 µg/g powder.

In one embodiment, the base hypoallergenic composition to which the combination of peptide(s) and TGF-β is added may contain as a source of nitrogen, peptides or free amino acids and, particularly from milk proteins, from cow or goat or sheep, such as whey proteins, alpha-lactalbumin, β-lactoglobulin, bovine serum albumin, casein acid, caseinates, or alpha, beta, kappa-casein, for example. The source of nitrogen can provide at least 7 to 25% of the total energy.

Vitamins and minerals are examples of typical dietary supplements. In a preferred embodiment, the composition is administered together with other compounds that enhance the described effect on the immunity of the young mammal. Such compounds can be other active compounds that synergistically or separately influence the immune response of the infant and/or potentiate the effect of the peptides, such as probiotics and prebiotics.

Examples of known probiotic compounds are *Bacillus, Bifidobacterum, Lactobacillus Saccharomyce, Streptococcus thermophilus, E. Faecium, E. Coli Nissle*. In particular, probiotics and non-replicating probiotics, such as the genus *Lactobacillus, Bifidobacterium* or combination thereof, for example *Lactobacillus paracasei, Lactobacillus rhamnosus, Bifidobacterium longum, Bifidobacterium lactis, Bifidobacterium breve*, or combination thereof, and applications of these bacteria.

Prebiotics and further ingredients are preferably selected from 2'Fucosyllactose, Lacto-difucotetraose, 3Fucosyllactose, Lacto-N-fucopentaose I, Lacto-N-fucopentaose II, Lacto-N-fucopentaose III, Lacto-N-neotetraose, Lacto-N-tetraose, 3'Sialyllactose, 6'Sialyllactose, 3'Sialyllacto-N-tetraose, 6'Sialyl-Lacto-N-neotetraose, inulin, fructooligosaccharide (FOS), short-chain fructooligosaccharide (short chain FOS), galacto-oligosaccharide (GOS), xylooligosaccharide (XOS), ganglioside, partially hydrolyzed guar gum, acacia gum, soybean-gum, or mixtures thereof.

Other carbohydrates may be present such as a second carbohydrate acting in synergy with the first carbohydrate and that is selected from the group consisting of xylooligosaccharide (XOS) gum, acacia gum, starch, partially hydrolyzed guar gum or mixtures thereof. The carbohydrate or carbohydrates may be present at about 1 g to 20 g or 1% to 80% or 20% to 60% in the daily doses of the composition. Alternatively, the carbohydrates are present at 10% to 80% of the dry composition.

In one embodiment, the nutritional composition comprises a mix of oligosaccharides according to WO2007/090894 (general teaching and specifically Example 1). It may be in particular used in combination with GOS. The base formula may provide an oligosaccharide mixture which comprises 5-70 wt % of at least one N-acetylated oligosaccharide selected from the group comprising GalNAcα1,3Galβ1,4Glc and Galβ1,6GalNAcα1,3Galβ1,4Glc, 20-90 wt % of at least one neutral oligosaccharide selected from the group comprising Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc.

One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition.

One or more food grade emulsifiers may be included in the nutritional composition if desired; for example diacetyl tartaric acid esters of mono- and di-glycerides, lecithin and mono- or di-glycerides or a mixture thereof. Similarly suitable salts and/or stabilisers may be included. Flavours can be added to the composition.

The combination of peptide(s) and TGF-β may be incorporated into or be present in a composition that is an infant "preterm formula" for infants born before term or has a low birth weight, a "starter formula" or a "follow-on formula". An example of such starter formula is given in Example 2.

Example 1

In vivo experiments to investigate the effect of the administration of a composition comprising peptides with sequences SEQ no. ID 1-8 and TGF-β at weaning to rat pups were carried out. Specifically, the protection of the mouse pups against food allergy after administration of the composition was measured.

The experiment was designed to exploit the fact that transient prevention of food allergy can be induced by ovalbumin (OVA) transfer through breast milk by OVA exposed and immunized mothers. The effect of administration after weaning of a partially hydrolyzed infant formula NAN®-HA or TGF-β enriched NAN®-HA formula on maintenance of food allergy protection was assessed at 12 weeks.

Two independent experiments (same setting) were performed testing the 6 following groups:
  Pups breastfed by nave mother and receiving the following regimen orally after weaning:
    water or NAN®-HA formula or TGF-β enriched NAN®-HA formula
  Pups breastfed by OVA-exposed and immunized mother and receiving the following regimen orally after weaning:
    water or NAN®-HA formula or TGF-β enriched NAN®-HA formula In Experiment 1, there were 6 mice per group and in Experiment 2, 10-11 mice per group.

Briefly, mice were immunized or not with OVA adsorbed on alum by two intraperitoneal injections, before mating. At delivery, nave pups were fostered by nave or immunized mother, receiving orally 2 mg of OVA three times a week, during three weeks (lactation period). At three weeks, mice are weaned and when 12 weeks old, mice were submitted to a protocol of food allergy induction (modified from Brandt et al. 2003) consisting briefly in OVA (50 ug)/Alum (1 mg) intraperitoneal injection at weeks 13 and 15, followed by intragastric OVA (50 ug) challenges, starting at week 17 and three times a week.

The mice were sacrificed when more than 50% of mice show diarrhea in the control group (naïve mother, water after weaning).

Food allergy was determined according to diarrhea score one hour after the challenge:
0: nomal/hard stools
1: soft/sticky/well-formed stools
2: not formed stools
3: one episode of liquid diarrhea
4: 2 or more episodes of liquid diarrhea Results were compared using Mann-Whithney non parametric test and are shown in FIG. 1.

Example 2

An example of the composition of an infant formula for use according to the present invention is given below. This composition is given by way of illustration only.

| Nutrient | Per 100 kcal | Per litre |
| --- | --- | --- |
| Energy | 100 | 670 |
| Partially Hydrolyzed Protein including peptides 1-8 (g) | 1.9 | 12.7 |
| Fat (g) | 5.3 | 35.7 |
| WPI (enriched in TGF-β) (mg) | 5.1 | 34.1 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| B. lactis | $1 \times 10^7$ cfu/g of powder | |

The invention claimed is:

1. A method for induction and maintenance of oral tolerance to β-lactoglobulin (BLG) and maintenance of oral tolerance to other food proteins that has been acquired via consumption of maternal mill in a young mammal during and after weaning period, the method comprising administering to the young mammal a composition comprising at least eight different peptides; each having a length from five to twelve amino adds that comprises a sequence selected from SEQ ID No. 1-8, and the composition further comprising transforming growth factor-beta (TGF-β), wherein each of SEQ ID NOs: 1-8 is present in the composition.

2. A method for primary prevention of allergic reactions to milk proteins and to electedly introduced dietary protein in a young mammal during and after weaning, the method comprising administering to the young mammal a composition comprising at least eight different peptides, each having a length from five to twelve amino adds that comprises a sequence selected from SEQ ID No. 1-8, and the composition further comprising TGF-β-β), wherein each of SEQ NOs: 1-8 is present in the composition.

3. The method according to claim 1, wherein the young mammal is a human infant or toddler.

4. The method according to claim 1, wherein the young mammal has been fed maternal milk from a mother who has been exposed to an ingredient selected from the group consisting of milk, egg, nut, peanut, shellfish, wheat, soy, and any other food protein during the feeding period.

5. The method according to claim 1, wherein the young mammal is at risk of developing allergy.

6. The method according to claim 1, wherein the young mammal is a companion animal.

7. The method according to claim 2, wherein the young mammal is a human infant or toddler.

8. The method according to claim 2, wherein the young mammal has been fed maternal milk from a mother who has been exposed to an ingredient selected from the group consisting of milk, egg, nut, peanut, shellfish, wheat, soy, and any other food protein during the feeding period.

9. The method according to claim 2, wherein the young mammal is at risk of developing allergy.

10. The method according to claim 2, wherein the young mammal is a companion animal.

* * * * *